United States Patent [19]

Kim

[11] Patent Number: 5,049,384

[45] Date of Patent: Sep. 17, 1991

[54] ANTIBACTERIAL COMPOSITION FOR MEDICAL USE AND A PROCESS FOR THE PREPARATION THEREOF

[76] Inventor: Young S. Kim, Cosmos Mansion 1002, #302-62, Ichon-Dong, Yongsan-Ku, Seoul, Rep. of Korea

[21] Appl. No.: 376,588

[22] Filed: Jul. 7, 1989

[30] Foreign Application Priority Data

Jul. 8, 1988 [KR] Rep. of Korea ............... 88-8503[U]

[51] Int. Cl.⁵ .................................................. A61K 9/00
[52] U.S. Cl. .................................... 424/405; 424/422; 424/451; 424/464; 424/489
[58] Field of Search ................ 424/451, 404, 484–489, 424/408, 409, 422, 464

[56] References Cited

U.S. PATENT DOCUMENTS 4,503,040  3/1985  Barth ................................... 424/114

FOREIGN PATENT DOCUMENTS 1081093  8/1967  United Kingdom .

OTHER PUBLICATIONS

Chemical Abstracts, 83 (11):97280r.
Antimicrobial Agents and Chemotherapy 15, No. 2 171–176 (1979) FU. K.P. and NEU, H. C.
J. Antimicrobial Chemotherapy 10, 117–123 (1982).

*Primary Examiner*—Thurman Page
*Attorney, Agent, or Firm*—Birch, Stewart, Kolasch & Birch

[57]  ABSTRACT

A pharmaceutical composition of sulbactam or pharmaceutically acceptable salts thereof and methampicillin or pharmaceutically acceptable salts thereof, in an amount of about 1–99% to 99–1% by weight. The pharamaceutical composition is effective for treating bacterial infections.

9 Claims, No Drawings

ANTIBACTERIAL COMPOSITION FOR MEDICAL USE AND A PROCESS FOR THE PREPARATION THEREOF

BACKGROUND OF THE INVENTION

1. Field of the Invention

The present invention relates to an antibacterial composition for medical use and a process for the preparation thereof. More particularly, the present invention relates to a synergistic composition which comprises 3,3-dimethyl-7-oxo-4-thia-1-azabicyclo (3.2.0)heptane-2-carboxylicacid, 4-4-dioxide[2S-(2α,5α)](sulbactam) or pharmaceutically acceptable salts thereof and 6-[D-(-)-α-(methylene aminophenylacetamido)]-penicillanic acid (methampicillin) or pharmaceutically acceptable salts thereof.

2. Description of the Prior Art

Sulbactam (penicillanic acid 1,1-dioxide) or pharmaceutically acceptable salts thereof are well known in the art as a kind of β-lactamase-resistance antibiotic. Although sulbactam or pharmaceutically acceptable salts thereof alone are a poor inhibitor of β-lactamases, when sulbactam or pharmaceutically acceptable salts thereof are combined with β-lactamase inhibiting antibiotics, the composition exhibits a modest increase in inhibition of the enzymatic hydrolysis of antibiotics [FU, K.P. and NEU, H.C., Comparative Inhibition of β-lactamase by novel β-lactam compounds. *Antimicrobial Agents and Chemotherapy* 15, No.2, 171–176 (1979)].

Methampicillin and its salts are disclosed in U.K. Patent No. 1,081,093 and have a marked increase in inhibition against gram-positive and gram-negative bacteria.

When the penicillanic acid sulphnone, sulbactam, and an effective amount of clavulanic acid are used with penicillin derivatives, or cephalosporin derivatives, the β-lactamase inhibiting activity thereof exhibits a modest increase in inhibition against *Escherichia coli* [Greenwood, D. and Eley, A.: In-Vitro evaluation of sulbactam, a penicillanic acid sulfone with β-lactam inhibitory properties. *J. Antimicrobial Chemotherapy* 10, 117–123 (1982)]

Pharmaceutical compositions comprising β-lactamose inhibitors are disclosed in U.S. Pat. No. 4,503,040. While the compounds are effective in enhancing the activity of B-lactam antibiotics in general, their preferred use is found in their combination with a penicillin or cephalosporin of established clinical utility, viz., amoxicillin, ampicillin, apalacillin, azlocillin, azthreonam, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefmenoxime, cefonicid, cefodizime, cefoperazone, ceforanide, cefotaxime, cefotiam, cefotetan, cefoxitin, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, furazlucillin, hetacillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin or ticarcillin, or a pharmaceutically acceptable salt thereof. However, a pharmaceutical composition of sulbactam combined with methampicillin has never been disclosed in the art and also the marked increase in activity of the composition in treating bacterial infections has never been disclosed.

SUMMARY OF THE INVENTION

Accordingly, it is an object of the present invention to provide an antibacterial composition for medical use and a process for the preparation thereof.

Another object of the present invention is to provide a composition which comprises sulbactam or a pharmaceutically acceptable salt thereof and methampicillin or a pharmaceutically acceptable salt thereof.

A further object of the present invention is to provide a pharmaceutical composition for treating bacterial infections which comprises in a weight ratio of about 1:99 to 99:1, of sulbactam or a pharmaceutically acceptable salt thereof and methampicillin or a pharmaceutically acceptable salt thereof.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a pharmaceutical composition comprising as components thereof sulbactam or a pharmaceutically acceptable salt thereof and methampicillin or a pharmaceutically acceptable salts thereof, said components being present in an amount of about 1-99% to 99-1% by weight. The present composition is effective in the treatment of bacterial infections.

DESCRIPTION OF THE PREFERRED EMBODIMENTS

Referring now in detail to the present invention, there is provided an antibacterial composition for medical use which comprises sulbactam or a pharmaceutically acceptable salt thereof and methampicillin or a pharmaceutically acceptable salt thereof, and a process for the preparation thereof.

The present invention is directed to a pharmaceutical composition which comprises sulbactam, 3.3-dimethyl-7-oxo-4-thia-1-azabicyclo(3.2.0)heptane-2-carboxylic acid, 4-4-dioxide [2S(2α,5α)]having the following formula (I):

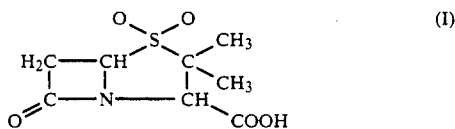

and methampicillin, 6-[D(-)-α-(methylene aminophenylacetamido)]-pencillanic acid having the following formula (II):

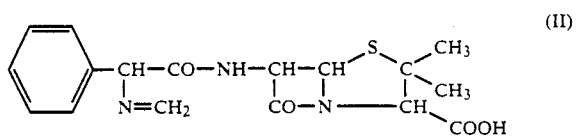

Sulbactam or pharmaceutically acceptable salts thereof and methampicillin or pharmaceutically acceptable salts thereof are present in a composition in an amount of about 1-99% to 99.-1% by weight, preferably in an amount of about 30-70% to 70-30% by weight.

In process for the preparation of the composition of the present invention, sulbactam or pharmaceutically acceptable salts thereof, such as the sodium salt thereof and methampicillin or pharmaceutically acceptable salts thereof, such as the sodium salt thereof are dissolved in equal amounts, in sterile distilled water. The initial mixture is filtered, and the resulting mixture is sterilized. At this time, a weight ratio in the range of 3:1 to 1:3 of sulbactam to methapicillin is preferable.

The β-lactamase inhibiting activity of the composition of sulbactam (I) and methampicillin (II) compared with that of piperacillin (III), cefotaxime (IV), or cephradine (V) is illustrated as follows:

1. MATERIALS AND METHODS (1) Name of Standard Bacterial Strains

As shown in Table I, enzymes isolated from a clinical source, Yoido Mary's Hospital, Seoul, Korea, are cultivated. Thereafter, all strains are tested in conventional minimum inhibitory concentration (MIC) tests using the agar dilution method.

TABLE I

| Name of standard strains and number | |
|---|---|
| Strains | No. |
| Staphylococcus aureus | 25 |
| Escherichia coli | 8 |
| Pseudomonas aeruginosa | 21 |
| Klebsiella pneumoniae | 9 |
| Serratia marcescens | 3 |
| Staphylococcus epidermidis | 2 |
| Enterobacter cloacae | 9 |
| Proteus vulgalis | 1 |
| Proteus mirabilis | 1 |
| actinobacter calcoaceticus | 1 |

2. ANTIBIOTICS

Sulbactam (I) and methampicillin (II), piperacillin (III), cefotaxime (IV), or cephradine (V) are respectively dissolved in sterile distilled water, the initial mixture filtered, and the resultant mixture sterilized.

3. INHIBITING ACTIVITY EXPERIMENT BY MEANS OF MIC METHOD

The experiment by means of MIC method uses a solid solution method [Chemotherapy 29, 76-79 (1981)]as follows:

(1) MIC Assay of Compounds (II), (III), (IV), and (V)

Serial dilutions of the above-four antibiotics, compounds (II), (III), (IV), and (V) are prepared in NB agar plates having 100, 8, 4, 2, 1, and 0.1 mcg/ml, respectively, and each agar plate is divided according to the number of strains. The strains to be tested are streaked on the plates and broth cultures are cultivated at 37° C. overnight. A concentration of the antibiotic compound of the last plate not having grown a strain is taken as a MIC.

(2) MIC Assay Compound (I)

Serial dilutions of compound (I), sulbactam, are prepared in NB agar plates having 128, 64, 32, 16, 8, 4, 2, 1, 0.1 mcg/ml, respectively, and each agar plate is divided according to the number of strains. The strains to be tested are streaked on the plates and broth cultures are cultivated overnight. Thereafter, the MIC of each plate is assayed.

4. INHIBITING ACTIVITY EXPERIMENT OF THE COMPOSITIONS

The composition of compound (I), sulbactam, and compounds (II), (III), (IV), and (V) are prepared. Serial dilution of 4 compounds (II) (III), (IV), and (V) are prepared in agar plates having 100, 16, 8, 4, 2, 1, and 0.1 mcg/ml. Compound (I) having 16 mcg/ml in equivalent with one fourth of MIC, is mixed with the above twenty eight serial dilution plates of 4 compounds (II), (III), (IV), and (V). A separate plate having only 16 mcg/ml of compound (I) is prepared. These plates are divided according to the number of strains and all strains to be tested are streaked on the plates overnight and broth cultures are performed.

5. RESULTS (1) MIC of Four Compounds Against Standard Strains

Table II shows MIC of four compounds against standard strains as follows:

TABLE II

| | MIC of compounds (II) (III) (IV) and (V) against standard strains | | | |
|---|---|---|---|---|
| Strains | comp. II | comp. III | comp. IV | comp. V |
| S. aureus | 1 | 1 | 2 | 2 |
| E. coli | 4 | 4 | 100 | 0.1 |
| Kl. pneumoniae | 100 | 100 | 100 | 0.1 |
| Ser. marcescens | 100 | 100 | 100 | 2 |
| S. epidermidis | 16 | 16 | 1 | 1 |
| Ent. cloacae | 8 | 2 | 100 | 2 |
| Pro. vulgalis | 1 | 1 | 100 | 0.1 |
| Pro. mirabilis | 1 | 1 | 100 | 0.1 |
| Ps. aeruginosa | 100 | 4 | 100 | 16 |

The compound (III) exhibited high orders of inhibitory activity against S. aureus, E. coli, S. epidermidis, Ent. cloacae, Pro. vulgalis, Pro. mirabilis, and Ps. aeruginosa.

The compound (II) exhibited high orders of inhibitory activity against the same above strains. However, the compound (II), methampicillin exhibited a marked increase in inhibitory activity against Ps. aeruginosa.

The compound (IV) exhibited high orders of inhibitory activity against S. aureus, and S. epidermidis.

The compound (V) exhibited high orders of inhibitory activity against S. aureus, E. coli, Kl. pneumoniae, Ser. marcescens, S. epidermidis, Ent. cloacae, Pro. vulgalis, Pro. mirabilis, and Ps. aeruginosa.

(2) MIC of Compound (I) Against Sixty-Eight Select Strains

The capacities of compound (I) to inhibit MIC against 68 select strains are shown in Table (III), (IV), (V), and (VI) as follows:

TABLE III

| Comparative activities of compound (II), compound (I), and composition (I) plus (II) against compound (II) - resistant strains | | | | |
|---|---|---|---|---|
| Strains | | comp. II | comp. I | compos. I + II |
| S. aureus | A. 6588 P | 1 | 128 | 1 |
| S. aureus | A | 100 | >128 | 1 |
| | D | 100 | >128 | 1 |
| | E | 16 | 128 | 1 |
| | F | 100 | 128 | 1 |
| | G | 100 | 128 | 2 |
| | H | 100 | >128 | 16 |
| E. coli | A. 25922 | 4 | 64 | 1 |

TABLE III-continued

Comparative activities of compound (II), compound (I), and composition (I) plus (II) against compound (II) - resistant strains

| Strains | | comp. II | comp. I | compos. I + II |
|---|---|---|---|---|
| E. | A | >100 | 64 | 8 |
| | B | >100 | >128 | >100 |
| | C | 100 | 64 | 8 |
| | D | >100 | 64 | 100 |
| | E | 100 | 64 | 4 |
| | F | >100 | 64 | 16 |
| | G | >100 | 64 | 16 |
| | H | >100 | 64 | 16 |
| S. epidermidis | A.12228 | 16 | 64 | 1 |
| S. epidermidis | A | 100 | >128 | 8 |
| Ent. cloacae | H. 30-4 | 8 | 64 | 4 |
| Ent. cloacae | A | 100 | 64 | 100 |
| | B | >100 | 128 | 100 |
| | D | 100 | 128 | 16 |
| Ps. aeruginosa | A 27853 | 100 | 128 | 100 |
| Ps. aeruginosa | A | >100 | >128 | >100 |
| | B | >100 | >128 | >100 |
| | C | >100 | >128 | >100 |
| | D | >100 | >128 | >100 |
| | E | >100 | >128 | >100 |
| | F | >100 | >128 | >100 |
| | G | >100 | >128 | >100 |
| | H | >100 | >128 | >100 |
| | I | >100 | >128 | >100 |
| | J | >100 | >128 | >100 |
| | K | >100 | >128 | >100 |
| | L | >100 | >128 | >100 |

TABLE IV

Comparative activities of compound (III), compound (I), and composition (I) plus (III) against compound (III) -resistant strains

| Strains | | comp. III | comp. I | compos. I + III |
|---|---|---|---|---|
| S. aureus | A. 6588 P | 1 | 128 | 1 |
| S. aureus | A | 100 | >128 | 1 |
| | B | 8 | >128 | 1 |
| | C | 8 | >128 | 1 |
| | D | 100 | >128 | 1 |
| | E | >100 | 128 | 1 |
| | F | 8 | 128 | 1 |
| | G | 100 | 128 | 2 |
| | H | >100 | >128 | 100 |
| E. coli | A. 25922 | 4 | 64 | 1 |
| E. coli | A | 100 | 64 | 8 |
| | B | 100 | 128 | 100 |
| | C | 8 | 64 | 1 |
| | D | >100 | 64 | 1 |
| | E | 8 | 64 | 1 |
| | F | >100 | 64 | 2 |
| | G | >100 | 64 | 2 |
| | H | >100 | 64 | 2 |
| S. epidermidis | A.12228 | 16 | 64 | 1 |
| S. epidermidis | A | >100 | >128 | 8 |
| | B | 100 | >128 | 4 |
| Ent. cloacae | H. 30-4 | 2 | 64 | 1 |
| Ent. cloacae | B | 100 | 128 | 4 |
| | D | 100 | 128 | 4 |
| Ps. aeruginosa | 27853 | 4 | 128 | 4 |
| Ps. aeruginosa | A | >100 | >128 | 8 |
| | D | >100 | >128 | 4 |
| | E | >100 | >128 | 16 |
| | F | 16 | 128 | 4 |
| | G | >100 | >128 | 100 |
| | H | 16 | >128 | 4 |
| | I | >100 | >128 | 4 |
| | K | >100 | >128 | >100 |
| | L | 100 | >128 | 16 |

TABLE V

Comparative activities of compound (IV), compound (I), and composition (I) plus (IV) against compound (IV) - resistant strains

| Strains | | comp. IV | comp. I | compos. I + IV |
|---|---|---|---|---|
| S. aureus | A. 6588 P | 2 | 128 | 1 |
| S. aureus | A | 8 | >128 | 2 |
| | D | 8 | >128 | 4 |
| | G | 8 | 128 | 8 |
| | H | >100 | >128 | >100 |
| | I | 8 | 128 | 4 |
| | O | >100 | >128 | >100 |
| | S | 100 | 128 | >100 |
| S. epidermidis | A.12228 | 1 | 64 | >0.1 |
| S. epidermidis | A | 100 | >128 | 100 |
| Ps. aeruginosa | A. 27853 | >100 | 128 | >100 |
| Ps. aeruginosa | A | >100 | >128 | >100 |
| | B | >100 | >128 | >100 |
| | C | >100 | >128 | >100 |
| | D | >100 | >128 | >100 |
| | E | >100 | >128 | >100 |
| | F | >100 | >128 | >100 |
| | G | >100 | >128 | >100 |
| | H | 100 | >128 | >100 |
| | I | >100 | >128 | >100 |
| | J | >100 | >128 | >100 |
| | K | >100 | >128 | >100 |
| | L | >100 | >128 | >100 |
| | M | >100 | >128 | >100 |
| | N | >100 | >128 | >100 |
| | O | >100 | >128 | >100 |
| | Q | >100 | >128 | >100 |
| | R | >100 | >128 | >100 |
| | S | >100 | >128 | >100 |
| | T | >100 | >128 | >100 |
| Pro. vulgalis | A. 6059 | 100 | 128 | 100 |
| Pro. vulgalis | A | 100 | 128 | 16 |
| Ser. marcescens | YH. S3 | >100 | 64 | >100 |
| Ser. marcescens | A | >100 | 64 | >100 |
| Pro. mirabilis | A. 25933 | 100 | 64 | >100 |
| Pro mirabilis | A | >100 | 64 | >100 |
| actinobacter calcoaceticus | A | >100 | 128 | 16 |

TABLE VI

Comparative activities of compound (V), compound (I), and composition (I) plus (V) against compound (V) -resistant strains

| Strains | | comp. V | comp. I | compos. I + V |
|---|---|---|---|---|
| S. aureus | A. 6588 P | 2 | 128 | 1 |
| S. aureus | H | >100 | >128 | 100 |
| | O | >100 | >128 | >100 |
| | R | >100 | >128 | >100 |
| S. epidermidis | A.12228 | 1 | 64 | 1 |
| S. epidermidis | A | 16 | >128 | 16 |
| Ps. aeruginosa | A. 27853 | 16 | 128 | 16 |
| Ps. aeruginosa | A | 100 | >128 | 100 |
| | B | 100 | >128 | 100 |
| | C | 100 | >128 | 100 |
| | D | 100 | >128 | 100 |
| | E | >100 | >128 | 100 |
| | F | >100 | >128 | 100 |
| | G | 100 | >128 | 100 |
| | H | 100 | 128 | 100 |
| | I | 100 | >128 | 100 |
| | J | 100 | >128 | 100 |
| | K | >100 | >128 | >100 |
| | L | >100 | >128 | >100 |
| | M | >100 | >128 | >100 |
| | N | >100 | >128 | >100 |
| | O | 100 | >128 | 100 |
| | P | >100 | >128 | >100 |
| | Q | >100 | >128 | 100 |
| | R | >100 | >128 | 100 |
| | S | >100 | >128 | >100 |
| | T | 100 | >128 | 100 |
| Ser. marcescens | YH. S3 | 2 | 64 | 2 |
| Ser. marcescens | A | 100 | 64 | 100 |
| Ent. cloacae | H30-4 | 2 | 128 | 1 |

TABLE VI-continued

Comparative activities of compound (V), compound (I), and composition (I) plus (V) against compound (V)-resistant strains

| Strains | | comp. V | comp. I | compos. I + V |
|---|---|---|---|---|
| Ent. cloacae | E | 100 | 128 | 4 |
| | F | 8 | 128 | 8 |
| | G | 100 | 128 | 8 |
| | H | 100 | 128 | 4 |
| | I | 100 | 128 | 100 |
| actinobacter calcoaceticus | A | 100 | 128 | 0.1 |

The MIC of compound (I) exhibited 128 mcg/ml at 64 mcg/ml against 68 select strains. That is, 16 strains showed 64 mcg/ml of MIC, 23 strains showed 128 mcg/ml, and 29 strains showed over 128 mcg/ml.

(3) MIC of Compositions

Since compound (I) does not exhibit β-lactamase inhibiting activity at 16 mcg/ml of MIC, in equivalent with one fourth concentration of MIC, the compounds (II), (III), (II), and (V) are combined with the compound (I) having 16 mcg/ml of MIC. Thereafter, MIC of the compositions are assayed.

As shown in Table (III), 14 strains in all 30 strains exhibited a reduction to a minimum of 4 times and maximum of 100 times of MIC. Particularly, the composition (I) plus (II) exhibited a marked increase in inhibition against *S. aureus and E. coli*.

As shown in Table (III), 23 strains in all 33 strains exhibited a reduction to a minimum of 4 times and maximum of 100 times of MIC. Particularly, 7 strains in 8 strains exhibited to reduce MIC against *S. aureus and E. coli*.

As shown in Table (IV), 2 strains in all 31 strains exhibited a reduction in MIC. That is, one strain exhibited a reduction of 4 times of MIC against *S. aureus* and the other strain exhibited a reduction of 16 times of MIC against *actinobacter calcoaceticus*.

As shown in Table (V), 4 strains in all 30 strains exhibited a reduction to a minimum of 12 times and maximum of 100 times of MIC.

Accordingly, β-lactam antibiotics have exhibited an excellent inhibitory activity compared with other antibiotics. However, since most strains of bacteria create β-lactamases, the bacteria has a tolerance against the β-lactam-antibiotics. Therefore, in order to solve this problem, one must use quite different antibiotics and the other combines the β-lactam antibiotics with β-lactamase inhibiting antibiotics, so as to resist the activities of β-lactamases thereof.

In the comparative experiments according to the present invention, the compounds (II), (III), (IV), and (V) are combined with the sulbactam of compound (I) to produce the desired compositions. Accordingly, the compositions, compounds (I), (II), (III), and (IV) are comparatively assayed by means of MIC. At this time, the concentration of the compound (I) is adjusted to have 16 mcg/ml in equivalent with one fourth of MIC, which does not exhibit its activity.

In the present invention, the synergistic composition of the sulbactam with methampicillin or a pharmaceutically acceptable salt thereof functions the same as that of clavulanic acid combined with β-lactam antibiotic. That is, the composition of sulbactam and methampicillin, exhibits a marked increase in inhibition against *S. aureus and E. coli* such as, in all 9 strains; i.e., 9 strains exhibited an excellent antibacterial activity against *S. aureus* and 7 strains exhibited an excellent antibacterial activity against *E. coli*.

The composition combining compound (I) with compound (IV) shows similar results to that of the composition combining compound (I) with compound (II). The compounds combining compound (I) with compound (IV) or with compound (V) shows lower activity than the above compositions combining the compound (II) or (III).

When using the present antibacterial composition of the sulbactam and methampicillin for bacterial infections in treating mammals, particularly man, the composition is administrated alone, or mixed with pharmaceutically acceptable carriers or diluents. The carrier or diluent is chosen on the basis of the intended mode of administration. For preferred, oral administration, tablets, capsules, lozenges, trochees, powders, syrups, elixirs, aqueous solutions and suspensions, and the like are used, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium sterate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying or suspending agents. If desired, certain sweetening an/or flavoring agents can be added. For parental administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

When using the composition according to the present invention to control bacterial infections, the daily dosage will be similar to that of other clinically used beta lactam antibiotics. Although the prescribing physical will ultimately decide the dosage to be used in a human subject, the composition will normally be used in an amount of 1.5 g (0.5 g sulbactam as the sodium salt and 1 g methamicillin as the sodium salt) as a daily adult dosage, for intramuscular injection. In some instances, the prescribing physician will determine that dosages outside these limits may be needed.

The present invention will now be described in more detail in connection with the following examples which should be considered as being exemplary and not limiting the present invention.

| Preparation 1 for capsule | |
|---|---|
| methampicillin as the sodium salt | 2 g |
| sulbactam as the sodium salt | 1 g |
| magnesium stearate | 8 mg |
| lactose | 4 g |

The above-ingredients are mixed and the mixture are filled into empty capsules in a conventional manner.

| Preparation 2 for injection | |
|---|---|
| methampicillin as the sodium salt | 2 g |
| sulbactam as the sodium salt | 1 g |
| sterile distilled water | 20 cc |
| Preparation 3 for injection | |
| methampicillin as the sodium salt | 1 g |
| sulbactam as the sodium salt | 0.5 g |
| sterile distilled water | 10 cc |

The above-ingredients of preparations 2 and 3 are dissolved in injection distilled water, filled in 5 cc and 10 cc vials respectively, and sterilized in a conventional manner.

| Preparation 4 for injection | |
|---|---|
| methampicillin as the sodium salt | 1 g |
| sulbactam as the sodium salt | 0.5 g |
| sterile distilled water | 10 cc |
| Preparation 5 for injection | |
| methampicillin as the sodium salt | 1 g |
| sulbactam as the sodium salt | 0.5 g |

The above-ingredients of preparations 4 and 4 are filled in 5 cc and 10 cc vials, respectively and sterilized in a conventional manner. When the user uses them, they are dissolved in distilled water to be used for injection.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A pharmaceutical composition for treating bacterial infections which comprises, in a weight ratio of 30:70 to 70:30 sulbactam or a pharmaceutically acceptable salt thereof and methampicillin or a pharmaceutically acceptable salt thereof.

2. A method for treating a bacterial infection caused by *Staphylococcus epidermidis* which comprises administering to a mammal an effective antibacterial amount of the composition according to claim 1.

3. The pharmaceutical composition of claim 1, wherein the pharmaceutically acceptable salt of sulbactam is sodium (2S,6R)-3,3-dimethyl-7-oxo-4-thia-1-azabicyclo(3.2.0)heptane-2-carboxylate, 4-4-dioxide.

4. The pharmaceutical composition of claim 1, wherein the pharmaceutically acceptable salt of methampicillin is sodium 6-[D-(-)-α-(methylene aminophenyllacetamido)]-penicillanate.

5. The method for treating a bacterial infection in a mammal which comprises administrating to said mammal an antibacterially effective amount of the pharmaceutical composition of claim 1.

6. The pharmaceutical composition of claim further containing a pharmaceutically acceptable diluent.

7. The pharmaceutical composition of claim 1 further containing a pharmaceutically acceptable carrier.

8. A method for treating a bacterial infection caused by *Staphylococcus aureus* which comprises administering to a mammal an effective antibacterial amount of the composition according to claim 1.

9. A method for treating a bacterial infection caused by *Escherichia coli* which comprises administering to a mammal an effective antibacterial amount of the composition according to claim 1.

* * * * *